US00PP23618P2

(12) United States Plant Patent
Barends

(10) Patent No.: US PP23,618 P2
(45) Date of Patent: May 21, 2013

(54) ***PELARGONIUM* PLANT NAMED 'FIPELSUMOR'**

(50) Latin Name: *Pelargonium×hortorum*
Varietal Denomination: Fipelsumor

(75) Inventor: Eveline Barends, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 13/317,163

(22) Filed: Oct. 11, 2011

(51) Int. Cl.
*A01H 5/00* (2006.01)

(52) U.S. Cl.
USPC ..... Plt./327

(58) Field of Classification Search ..... Plt./327
See application file for complete search history.

*Primary Examiner* — Susan McCormick Ewoldt
(74) *Attorney, Agent, or Firm* — C. A. Whealy

(57) ABSTRACT

A new and distinct cultivar of *Pelargonium* plant named 'Fipelsumor', characterized by its upright and outwardly spreading growth habit; rounded plant habit; freely basal branching habit; moderately vigorous growth habit; early and freely flowering habit; semi-double orange red-colored flowers; and good garden performance.

1 Drawing Sheet

Botanical designation: *Pelargonium×hortorum*.
Cultivar denomination: 'FIPELSUMOR'.

BACKGROUND OF THE INVENTION

The present invention relates to a new and distinct cultivar of *Pelargonium* plant, botanically known as *Pelargonium×hortorum*, commercially referred to as Zonal Geranium and hereinafter referred to by the name 'Fipelsumor'.

The new *Pelargonium* plant is a product of a planned breeding program conducted by the Inventor in De Lier, The Netherlands. The objective of the breeding program is to create new medium-sized, freely-branching and freely-flowering *Pelargonium* plants that are moderately vigorous, flower early and have attractive leaf and flower coloration.

The new *Pelargonium* plant originated from a cross-pollination made by the Inventor in October, 2005 in De Lier, The Netherlands of *Pelargonium×hortorum* 'Fisum Coral Red', disclosed in U.S. Plant Pat. No. 16,103, as the female, or seed, parent with a proprietary selection of *Pelargonium×hortorum* identified as code number 99992, not patented, as the male, or pollen, parent. The new *Pelargonium* plant was discovered and selected by the Inventor as a single flowering plant from within the progeny of the stated cross-pollination in a controlled greenhouse environment in De Lier, The Netherlands, in March, 2006.

Asexual reproduction of the new *Pelargonium* plant by vegetative terminal cuttings in a controlled greenhouse environment in De Lier, The Netherlands, since July, 2006 has shown that the unique features of this new *Pelargonium* plant are stable and reproduced true to type in successive generations.

SUMMARY OF THE INVENTION

Plants of the new *Pelargonium* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Fipelsumor'. These characteristics in combination distinguish 'Fipelsumor' as a new and distinct *Pelargonium* plant:

1. Upright and outwardly spreading growth habit; rounded plant habit.
2. Freely basal branching habit.
3. Moderately vigorous growth habit.
4. Early and freely flowering habit.
5. Semi-double orange red-colored flowers.
6. Good garden performance.

Plants of the new *Pelargonium* differ primarily from plants of the female parent, 'Fisum Coral Red', in flower color as plants of 'Fisum Coral Red' have dark orange-colored flowers. In addition, plants of the new *Pelargonium* have shorter peduncles than plants of 'Fisum Coral Red'.

Plants of the new *Pelargonium* differ primarily from plants of the male parent selection in flower form as plants of the male parent selection have single-type flowers.

Plants of the new *Pelargonium* can be compared to plants of *Pelargonium×hortorum* 'Toscana Gesa', not patented. In side-by-side comparisons conducted in De Lier, The Netherlands, plants of the new *Pelargonium* differed primarily from plants of 'Toscana Gesa' in plant size as plants of the new *Pelargonium* were shorter and not as vigorous as plants of 'Toscana Gesa'. In addition, plants of the new *Pelargonium* had darker-colored flowers than plants of 'Toscana Gesa'.

BRIEF DESCRIPTION OF THE PHOTOGRAPH

The accompanying colored photograph illustrates the overall appearance of the new *Pelargonium* plant showing the colors as true as it is reasonably possible to obtain in colored reproductions of this type. Colors in the photograph may differ slightly from the color values cited in the detailed botanical description which accurately describe the colors of the new *Pelargonium* plant. The photograph comprises a side perspective view of a typical flowering plant of 'Fipelsumor' grown in a container.

DETAILED BOTANICAL DESCRIPTION

The aforementioned photograph and following observations, measurements and values describe plants grown during the summer in 12-cm containers in De Lier, The Netherlands in a glass-covered greenhouse and under cultural practices which closely approximate commercial *Pelargonium* production. During the production of the plants, day temperatures ranged from 16° C. to 28° C. and night temperatures ranged from 14° C. to 18° C. Plants were ten weeks old when the photograph and the description were taken. In the detailed description, color references are made to The Royal Horticultural Society Colour Chart, 2007 Edition, except where general terms of ordinary dictionary significance are used.

Botanical classification: *Pelargonium×hortorum* 'Fipelsumor'.

Parentage:

*Female, or seed, parent.*—*Pelargonium×hortorum* 'Fisum Coral Red', disclosed in U.S. Plant Pat. No. 16,103.

*Male or pollen parent.*—Proprietary selection of *Pelargonium×hortorum* identified as code number 99992, not patented.

Propagation:

*Type.*—By vegetative terminal cuttings.

*Time to initiate roots, summer.*—About four days at temperatures of 22° C.

*Time to initiate roots, winter.*—About seven days at temperatures of 22° C.

*Time to produce a rooted young plant, summer.*—About 16 days at temperatures of 22° C. to 30° C.

*Time to produce a rooted young plant, winter.*—About three weeks at temperatures of 20° C. to 25° C.

*Root description.*—Medium in thickness, fibrous; whitish grey in color.

*Rooting habit.*—Moderately freely branching, medium density.

Plant description:

*Plant form and habit.*—Upright and outwardly spreading growth habit; rounded and uniformly mounded plant habit; densely foliated.

*Growth and branching habit.*—Moderately vigorous growth habit; freely basal branching habit with about three to four basal branches developing per plant.

*Plant height, to top of umbels.*—About 18 cm to 20 cm.

*Plant height, to top of foliar plane.*—About 10 cm.

*Plant width.*—About 20 cm.

*Lateral branches.*—Length: About 6 cm to 8 cm. Diameter: About 6 mm. Internode length: About 1 cm to 1.5 cm. Texture: Pubescent. Strength: Moderately strong. Color: Close to 144A.

Foliage description:

*Arrangement.*—Alternate; simple.

*Length (including petiole).*—About 3.5 cm to 4 cm.

*Width.*—About 5.5 cm to 6.5 cm.

*Shape.*—Orbicular.

*Apex.*—Acute.

*Base.*—Cordate.

*Margin.*—Crenate.

*Venation pattern.*—Palmate.

*Texture, upper surface.*—Smooth, glabrous.

*Texture, lower surface.*—Slightly pubescent; pubescence more dense along venation.

*Color.*—Developing leaves, upper surface: Close to N137B. Developing leaves, lower surface: Close to 147B. Fully expanded leaves, upper surface: Close to N137A; venation, close to N137A. Fully expanded leaves, lower surface: Close to 147B; venation, close to 146C. Zonation pattern: Location: Center of the leaf. Width: About 2 cm. Color: Darker than 147A.

*Petiole.*—Length: About 4 cm to 5 cm. Diameter: About 2 mm to 3 mm. Texture, upper and lower surfaces: Pubescent. Color, upper and lower surfaces: Close to 146A.

Flower description:

*Flower arrangement.*—Semi-double rotate flowers arranged in rounded hemispherical umbels arising from apical leaf axils; umbels displayed above the foliage on strong peduncles; flowers face upright to outwardly.

*Fragrance.*—None detected.

*Quantity of flowers.*—Freely flowering habit; about 28 to 30 flowers and 32 to 34 flower buds per umbel and about eight to ten umbels per plant.

*Flowering season.*—In The Netherlands, flowering is continuous from spring until frost in the autumn; early flowering habit, plants begin flowering about six to eight weeks after planting.

*Flower longevity.*—Depending on environmental conditions, individual flowers last about 2 to 14 days on the plant; flowers persistent.

*Umbel height.*—About 6.5 cm.

*Umbel diameter.*—About 8 cm.

*Flower diameter.*—About 4.5 cm by 4 cm.

*Flower depth (height).*—About 1.5 cm.

*Flower buds.*—Length: About 5 mm to 11 mm. Diameter: About 5 mm to 7 mm. Shape: Globular to elliptical. Color: Close to 146B; towards the base, close to 59B.

*Petals.*—Quantity per flower: About six to eight. Length: About 2 cm to 2.3 cm. Width: About 1.6 cm to 1.8 cm. Shape: Spatulate to obovate. Apex: Obtuse. Base: Attenuate. Margin: Entire. Texture, upper and lower surfaces: Smooth, glabrous; velvety. Color: When opening and fully opened, upper surface: Close to 33A; color does not fade with development. When opening and fully opened, lower surface: Close to 39B; towards the margins, close to 39A; color does not fade with development.

*Petaloids.*—Quantity per flower: Typically none, or if present usually only one. Length: About 1.5 cm. Width: About 1 cm. Shape: Irregularly shaped; obovate to irregularly oblanceolate. Apex: Obtuse. Base: Attenuate. Margin: Entire. Texture, upper and lower surfaces: Smooth, glabrous; velvety. Color: When opening and fully opened, upper surface: Close to 33A; color does not fade with development. When opening and fully opened, lower surface: Close to 39B; towards the margins, close to 39A; color does not fade with development.

*Sepals.*—Quantity per flower: Five arranged in a single whorl. Length: About 1 cm. Width: About 3 mm. Shape: Lanceolate to acicular. Apex: Acute. Base: Lobate to truncate. Margin: Entire. Texture, upper and lower surfaces: Densely pubescent. Color, upper and lower surfaces: Close to 146A to 146B.

*Peduncle (umbel stem).*—Length: About 12 cm to 14 cm. Diameter: About 3 mm to 4 mm. Strength: Strong. Angle: Erect to about 30° C. from vertical. Texture: Pubescent. Color: Close to 146B.

*Pedicel (individual flower stem).*—Length: About 2 cm to 2.2 cm. Diameter: About 1 mm. Strength: Moderately strong. Angle: Erect to about 60° C. from vertical. Texture: Pubescent. Color: Close to 146B.

*Reproductive organs*.—Androecium: Stamen quantity per flower: About six to eight. Filament length: About 6 mm to 7 mm. Filament color: Close to 155A. Anther length: About 2 mm to 3 mm. Anther shape: Oblong. Anther color: Close to 39A. Pollen amount: Moderate. Pollen color: Close to 33B. Gynoecium: Pistil quantity per flower: One. Pistil length: About 8 mm. Stigma shape: Tapering; reflexed. Stigma color: Close to 60A. Style length: About 1 mm to 2 mm. Style color: Close to 60B. Ovary color: Close to 146C.

*Fruits and seeds*.—Fruit and seed development have not been observed on plants of the new *Pelargonium*.

Disease/pest resistance: Plants of the new *Pelargonium* have not been observed to be resistant to pathogens and pests common to *Pelargoniums*.

Garden performance: Plants of the new *Pelargonium* have been observed to tolerate rain, wind, and temperatures ranging from about 1° C. to about 45° C. and have demonstrated good garden performance.

It is claimed:

1. A new and distinct *Pelargonium* plant named 'Fipelsumor' as illustrated and described.

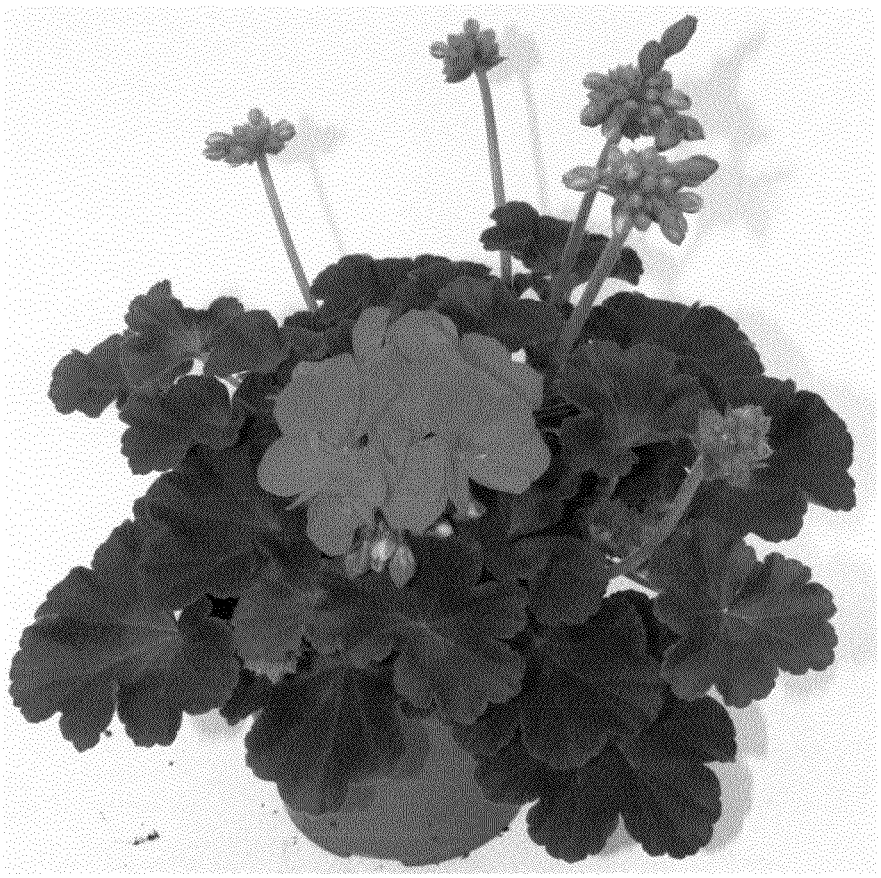

* * * * *